United States Patent [19]

Brown et al.

[11] 4,093,621

[45] June 6, 1978

[54] PROCESS FOR PREPARING HETEROCYCLICALKYLTHIOALKYL-N-CYANOGUANIDINES AND THIOUREAS

[75] Inventors: Thomas Henry Brown; Graham John Durant, both of Welwyn Garden City; John Colin Emmett, Codicote; Charon Robin Ganellin, Welwyn Garden City, all of England

[73] Assignee: Smith Kline & French Laboratories Limited, Welwyn Garden City, England

[21] Appl. No.: 741,586

[22] Filed: Nov. 15, 1976

Related U.S. Application Data

[62] Division of Ser. No. 606,269, Aug. 20, 1975, Pat. No. 4,013,678.

[30] Foreign Application Priority Data

Sep. 2, 1974 United Kingdom .............. 38257/74

[51] Int. Cl.² .................. C07D 213/44; C07D 233/30
[52] U.S. Cl. ..................... 260/294.8 H; 260/294.8 G; 260/302 R; 260/302 A; 260/302 D; 260/307 H; 260/308 R; 548/342

[58] Field of Search ................ 260/294.8 G, 294.8 H, 260/309, 308 R, 307 H, 302 R, 302 A, 302 D; 548/342

[56] References Cited

U.S. PATENT DOCUMENTS

3,905,984   9/1975   Durant et al. ................ 260/294.8 H

FOREIGN PATENT DOCUMENTS

1,338,169   11/1973   United Kingdom ......... 260/294.8 H

*Primary Examiner*—Alan L. Rotman
*Attorney, Agent, or Firm*—Joan S. Keps; Richard D. Foggio; William H. Edgerton

[57] ABSTRACT

Process for preparing heterocyclicalkylthioalkyl-N-cyanoguanidines and thioureas by treating a heterocyclicalkyl derivative with a mercaptoalkyl-N-cyanoguanidine or thiourea. Two specific products are N-cyano-N'-methyl-N''-[2-((5-methyl-4-imidazolyl)methylthio)ethyl]guanidine and N-methyl-N'-[2-((5-methyl-4-imidazolyl)methylthio)ethyl]thiourea, both useful as histamine $H_2$-antagonists.

8 Claims, No Drawings

PROCESS FOR PREPARING HETEROCYCLICALKYLTHIOALKYL-N-CYANOGUANIDINES AND THIOUREAS

This is a division of application Ser. No. 606,269 filed Aug. 20, 1975 now U.S. Pat. No. 4,013,678.

This invention relates to an improved chemical process. In particular it relates to an improved process for the production of certain pharmacologically active compounds.

In British Patent No. 1,338,169, thioureas and cyanoguanidines have been described including inter alia compounds of the following formula:

$$R_2-NH-C\underset{NHR_1}{\overset{E}{\diagup\!\!\!\diagdown}}$$

wherein E is sulphur or NCN, $R_1$ is hydrogen or lower alkyl such as methyl, and $R_2$ is a grouping of the structure shown in Formula II:

$$Het-(CH_2)_m-S-(CH_2)_n-$$

FORMULA II wherein Het is a nitrogen-containing 5 or 6 membered heterocyclic ring such as imidazole, pyridine, thiazole, isothiazole, oxazole, isoxazole, triazole or thiadiazole which is optionally substituted by lower alkyl, hydroxyl, halogen or amino: and $m$ is 1 or 2, and $n$ is 2 or 3 such that the sum of $m$ and $n$ is 3 or 4.

A number of processes for the production of compounds of Formula I were also described in British Patent No. 1,338,169. In particular there was disclosed a process which comprises the reaction of an amine of formula $R_2NH_2$, wherein $R_2$ has the same significance as in Formula I, with an isothiocyanate of formula $R_3NCS$ wherein $R_3$ is lower alkyl or acyl such as benzoyl to produce compounds of Formula I wherein E is sulphur.

Some disadvantages may be associated with the use of compounds of formula $R_3NCS$ in a chemical process.

It is an objective of the present invention to provide an alternative process for the production of compounds of Formula I wherein E is sulphur, wherein the use of isothiocyanates may be avoided and, as we have found that the mercapto group of mercaptoalkylthiourea compounds can be selectively alkylated, this provides the basis for such an alternative process. The present invention also relates to an alternative process for the production of compounds of Formula I wherein E is NCN.

Accordingly, we provide a process for the production of compounds of Formula I in which a compound of the following Formula III:

$$Het-(CH_2)_m-Z$$

FORMULA III wherein Het and $m$ have the same significance as in Formula II and Z is a group such that it forms a good leaving group for example halogen, substituted sulphonyloxy such as tosyloxy methanesulphonyloxy or trifluoromethanesulphonyloxy, substituted benzoyloxy with one or more electron-withdrawing substituents such as nitro or chloro, trifluoroacetoxy, or diarylphosphoryloxy, for example diphenyl-phosphonyloxy, is reacted with a compound of Formula IV:

$$HS-(CH_2)_n-NH-C\underset{NHR_1}{\overset{E}{\diagup\!\!\!\diagdown}}$$

wherein $n$, E and $R_1$ have the same significance as in Formula I, under basic conditions, for example in the presence of sodium ethoxide in ethanol, in the presence of potassium t-butoxide in t-butanol, or with sodium hydride in dimethylformamide.

Preferably, Z is chlorine, bromine, methanesulphonyloxy or tosyloxy, and particularly preferably chlorine. The compounds of Formula III may be prepared from the corresponding alcohols, which are known compounds, by standard chemical methods; for example, compounds of Formula III wherein Z is chlorine can be prepared from the corresponding alcohol and thionyl chloride and compounds of Formula III wherein Z is tosyloxy may be prepared by treating the corresponding alcohol with tosyl chloride in pyridine and, for example in the case of imidazole derivatives selectively removing the N-tosyl group under mild acidic conditions.

The compounds of Formula IV wherein E is NCN may be prepared from dimethylcyanodithioimidocarbonate by successive reaction with the amine $R_1NH_2$ and an amino-alkylmercaptan of formula $HS-(CH_2)_n-NH_2$.

It will be understood that many of the compounds produced and used as starting materials in the process of our invention may exist in the form of an acid addition salt.

The process of the present invention is particularly advantageous for the preparation of compounds of Formula I wherein the heterocyclic nucleus may be sensitive to treatment with acids, for example, when the heterocyclic nucleus is oxazole.

The process of the present invention is particularly useful when the compounds of Formula IV are such that $R_1$ is methyl or hydrogen.

The process for the production of those compounds of Formula I wherein $R_1$ is hydrogen and E is sulphur, is particularly advantageous over the process described in British Patent Specification No. 1,338,169 since the latter process involves a two-step method requiring the use of an acyl isothiocyanate and subsequent hydrolysis of the product.

The process of the present invention is advantageous for the production of compounds of Formula I wherein $R_2$ is Het-$CH_2$-S-$(CH_2)_2$- and is particularly preferred when Het is imidazole, thiazole, isothiazole or pyridine and is optionally substituted by methyl, chlorine or bromine. Specific compounds which may be made by the present process are the following:

N-methyl-N'-[2-((5-methyl-4-imidazolyl)methylthio)ethyl]-thiourea

N-methyl-N'-[2-(4-imidazolylmethylthio)ethyl]thiourea

N-methyl-N'-[2-((5-bromo-4-imidazolyl)methylthio)ethyl]-thiourea

N-methyl-N'-[2-((1-methyl-2-imidazolyl)methylthio)ethyl]-thiourea

N-methyl-N'-[2-((1-methyl-2-imidazolyl)methylthio)ethyl]-thiourea

N-methyl-N'-[2-((2-imidazolyl)methylthio)ethyl]thiourea

N-methyl-N'-[2-((2-thiazolyl)methylthio)ethyl]thiourea

N-methyl-N'-[2-((3-(1,2,4)-triazolyl)methylthio)ethyl]thiourea

N-methyl-N'-[2-(3-isothiazolylmethylthio)ethyl]thiourea

N-methyl-N'-[2-(3-isoxazolylmethylthio)ethyl]thiourea

N-methyl-N'-[2-((5-amino-2-(1,3,4)-thiadiazolyl)methylthioethyl]thiourea

N-ethyl-N'-[2-((5-methyl-4-imidazolyl)methylthio)ethyl]thiourea

N-[2-((5-methyl-4-imidazolyl)methylthio)ethyl]thiourea

N-cyano-N'-methyl-N''-[2-((5-methyl-4-imidazolyl)methylthio)-ethyl]guanidine

N-cyano-N'-ethyl-N''-[2-((5-methyl-4-imidazolyl)methylthio)-ethyl]guanidine

N-cyano-N'-methyl-N''-[2-((5-bromo-4-imidazolyl)methylthio)-ethyl]guanidine

N-cyano-N'-methyl-N''-[2-((2-thiazolyl)methylthio)ethyl]-guanidine

N-cyano-N'-methyl-N''-[2-((3-isothiazolyl)methylthio)ethyl]-guanidine

N-cyano-N'-methyl-N''-[2-((3-bromo-2-pyridyl)methylthio)ethyl]-guanidine.

N-cyano-N'-[2-((5-methyl-4-imidazolyl)methylthio)ethyl]-guanidine

As stated in British Patent No. 1,338,169, the compounds of Formula I (which may be produced by the present process) are pharmacologically active, for example, as histamine H$_2$-antagonists (see Nature 1972, 236, 385), and they are useful for example, as inhibitors of gastric acid secretion. For administration they will of course be made up in suitable pharmaceutically acceptable unit dosage forms.

The compounds of Formula I wherein E is sulphur are also useful as intermediates for the production of compounds of Formula I wherein E is NCN, for example, N-methyl-N'-[2-((5-methyl-4-imidazolyl)methylthio)ethyl]thiourea may be reacted with a heavy metal salt of cyanamide such as lead, mercury or cadmium cyanamide to yield N-cyano-N'-methyl-N''-[2-((5-methyl-4-imidazolyl)methylthio)ethyl]guanidine or N-methyl-N'-[2-((5-methyl-4-imidazolyl)methylthio)ethyl]-thiourea may be alkylated and the product reacted with cyanamide and a suitable strong base such as potassium t-butoxide to yield N-cyano-N'-methyl-N''-[2-((5-methyl-4-imidazolyl)methylthio)ethyl]guanidine.

Throughout this specification by the term "lower alkyl" we refer to an alkyl group having from 1 to 4 carbon atoms.

The invention is illustrated but in no way limited by the following examples:

EXAMPLE 1

N-Methyl-N$^1$-(2-mercaptoethyl)thiourea (3.85 g) in dry ethanol (10 ml) was added to a solution of sodium (1.18 g) in dry ethanol (50 ml) and the mixture was stirred at room temperature for one hour. 4-Chloromethyl-5-methylimidazole hydrochloride (4.29 g) was added portionwise over one hour to this stirred mixture at room temperature. The mixture was stirred at room temperature for a further hour and heated under reflux for ½ hour, cooled and filtered. The filtrate was evaporated to an oily solid which was recrystallised from water to give N-methyl-N$^1$-[2-((5-methyl-4-imidazolyl)methylthio)ethyl]-thiourea (3.2 g) m.p. 149°–151° C.

(Found: C, 44.0: H, 6.6: N, 22.7: S, 25.9: C$_9$H$_{16}$N$_4$S$_2$ requires: C, 44.2: H, 6.6: N, 22.9: S, 26.2%).

EXAMPLE 2

(i) A solution of cysteamine hydrochloride (5.68 g) in water (20 ml) was added to a suspension of N-cyano-N,S-dimethylisothiourea (6.46 g) in ethanol (100 ml). A solution of sodium hydroxide (4.0 g) in water (20 ml) was added to the mixture and the suspension was heated under reflux for one hour. The resulting clear solution was concentrated to remove ethanol, a little more water was added and the alkaline aqueous solution was extracted with ethyl acetate. The aqueous solution was adjusted to pH4 with hydrochloric acid and extracted with ethyl acetate. This latter organic extract was dried and evaporated to give N-cyano-N'-methyl-N''-(2-mercaptoethyl)guanidine (6.12 g) as a colourless oil.

In order to characterise this product a solution of 2,4-dinitrochlorobenzene (7.7 g) in 95% ethanol (50 ml) was added to a solution of N-cyano-N'-methyl-N''-(2-mercaptoethyl)guanidine (6.0 g) in 95% ethanol. The mixture was refluxed for one hour and cooled. The resulting crystalline solid (7.73 g) was collected and was triturated with a large volume of ether and was recrystallised from acetonitrile to afford N-cyano-N'-methyl-N''-[S-(2,4-dinitrophenyl)-2-mercaptoethyl]-guanidine, m.p. 210°–211° C.

Found: C, 41.0: H, 3.7: N, 26.0: S, 10.0: C$_{11}$H$_{12}$N$_6$O$_4$S requires: C, 40.7: H, 3.7: N, 25.9: S, 9.9%).

(ii) Sodium (1.43 g) was added, with stirring under nitrogen, to dry ethanol (100 ml). After the sodium had dissolved a solution of N-cyano-N'-methyl-N''-(2-mercaptoethyl)guanidine (4.90 g) in dry ethanol (50 ml) was added and the mixture was stirred at room temperature for one hour. 5-Methyl-4-chloromethylimidazole hydrochloride (5.18 g) was added in batches over a period of 1 hour at room temperature. The mixture was then stirred at room temperature, for a further hour and heated at reflux temperature for ½ hour. After cooling the mixture was filtered and the filtrate was evaporated to a glassy solid (8.8 g). This crude product was chromatographed on silica gel with acetonitrile as eluant and the solid product obtained (3.60 g) was recrystallised from acetonitrile to give N-cyano-N'-methyl-N''-[2-(5-methyl-4-imidazolylmethylthio)ethyl]guanidine, m.p. = 140°–142° C.

(Found: C, 47.9: H, 6.3: N, 33.3: S, 12.5: C$_{10}$H$_{16}$N$_6$S requires: C, 47.6: H, 6.4: N, 33.3: S, 12.7%)

EXAMPLE 3

Substitution of
(a) N-(2-mercaptoethyl)thiourea
(b) N-ethyl-N'-(2-mercaptoethyl)thiourea
(c) N-butyl-N'-(2-mercaptoethyl)thiourea
(d) N-methyl-N'-(2-mercaptopropyl)thiourea for N-methyl-N'-(2-mercaptoethyl)thiourea in the procedure of Example 1 leads to the production of
(a) N-[2-((5-methyl-4-imidazolyl)methylthio)ethyl]thiourea
(b) N-ethyl-N'-[2-((5-methyl-4-imidazolyl)methylthio)ethyl]thiourea
(c) N-butyl-N'-[2-((5-methyl-4-imidazolyl)methylthio)ethyl]thiourea
(d) N-methyl-N'-[3-((5-methyl-4-imidazolyl)methylthio)propyl]thiourea The starting materials may be prepared by published methods (see J. Org. Chem. 28, 3140 (1963) and 33, 884 (1968)), and methods directly analogous to published methods.

EXAMPLE 4

Substitution of
(a) N-cyano-N'-(2-mercaptoethyl)guanidine
(b) N-cyano-N'-ethyl-N''-(2-mercaptoethyl)guanidine
(c) N-cyano-N'-butyl-N''-(2-mercaptoethyl)guanidine
(d) N-cyano-N'-methyl-N''-(3-mercaptopropyl)guanidine
for N-cyano-N'-methyl-N''-(2-mercaptoethyl)guanidine in the procedure of Example 2(ii) leads to the production of (a)
(a) N-cyano-N'-[2-((5-methyl-4-imidazolyl)methylthio)ethyl]guanidine
(b) N-cyano-N'-ethyl-N''-[2-((5-methyl-4-imidazolyl)methylthio)ethyl]guanidine
(c) N-cyano-N'-butyl-N''-[2-((5-methyl-4-imidazolyl)methylthio)ethyl]guanidine
(d) N-cyano-N'-methyl-N''-[3-((5-methyl-4-imidazolyl)methylthio)propyl]guanidine The starting materials may be prepared by successively treating N-cyano dimethyldithioimidocarbonate with ammonia, methylamine, ethylamine or butylamine, and 2-mercaptoethylamine or 3-mercaptopropylamine.

EXAMPLE 5

Substitution of
(a) 4-(chloromethyl)imidazole
(b) 4-(chloromethyl)-5-bromoimidazole
(c) 2-(chloromethyl)-1-methylimidazole
(d) 2-(chloromethyl)imidazole
(e) 2-(chloromethyl)thiazole
(f) 3-(chloromethyl)-(1,2,4)triazole
(g) 3-(chloromethyl)isothiazole
(h) 3-(chloromethyl)isoxazole
(i) 2-(chloromethyl)-5-amino-(1,3,4)thiadiazole
(j) 2-(chloromethyl)-3-methylpyridine
(k) 2-(chloromethyl)-3-chloropyridine
(l) 2-(chloromethyl)-3-bromopyridine
(m) 2-(chloromethyl)-3-hydroxypyridine
(n) 4-(2-chloroethyl)imidazole
for 4-chloromethyl-5-methylimidazole in the procedure of Example 1 leads to the production of
(a) N-methyl-N'-[2-(4-imidazolylmethylthio)ethyl]thiourea
(b) N-methyl-N'-[2-((5-bromo-4-imidazolyl)methylthio)-ethyl]thiourea
(c) N-methyl-N'-[2-((1-methyl-2-imidazolyl)methylthio)-ethyl]thiourea
(d) N-methyl-N'-[2-((2-imidazolyl)methylthio)ethyl]-thiourea
(e) N-methyl-N'-[2-((2-thiazolyl)methylthio)ethyl]thiourea
(f) N-methyl-N'-[2-((3-(1,2,4)-triazolyl)methylthio)ethyl]thiourea
(g) N-methyl-N'-[2-(3-isothiazolylmethylthio)ethyl]thiourea
(h) N-methyl-N'-[2-(3-isoxazolylmethylthio)ethyl]thiourea
(i) N-methyl-N'-[2-((5-amino-2-(1,3,4)-thiadiazolyl)methylthioethyl]thiourea
(j) N-methyl-N'-[2-((3-methyl-2-pyridyl)methylthio)ethyl]thiourea
(k) N-methyl-N'-[2-((3-chloro-2-pyridyl)methylthio)ethyl]thiourea
(l) N-methyl-N'-[2-((3-bromo-2-pyridyl)methylthio)ethyl]-thiourea
(m) N-methyl-N'-[2-((3-hydroxy-2-pyridyl)methylthio)ethyl]thiourea
(n) N-methyl-N'-[2-(4-imidazolylethylthio)ethyl]thiourea The starting materials are either known compounds or may be prepared from the corresponding hydroxymethyl derivatives by standard methods e.g., treatment with thionyl chloride or from alkoxymethyl derivatives by ether cleavage e.g., with hydrobromic acid and treatment of the product with thionyl chloride.

EXAMPLE 6

Substitution of
(a) 4-(chloromethyl)imidazole
(b) 4-(chloromethyl)-5-bromoimidazole
(c) 2-(chloromethyl)-1-methylimidazole
(d) 2-(chloromethyl)imidazole
(e) 2-(chloromethyl)thiazole
(f) 3-(chloromethyl)-(1,2,4)triazole
(g) 3-(chloromethyl)isothiazole
(h) 3-(chloromethyl)isoxazole
(i) 2-(chloromethyl)-5-amino-(1,3,4)thiadiazole
(j) 2-(chloromethyl)-3-methylpyridine
(k) 2-(chloromethyl)-3-chloropyridine
(l) 2-(chloromethyl)-3-bromopyridine
(m) 2-(chloromethyl)-3-hydroxypyridine
(n) 4-(2-chloroethyl)imidazole
for 4-chloromethyl-5-methylimidazole in the procedure of Example 2(ii) leads to the production of
(a) N-cyano-N'-methyl-N''-[2-(4-imidazolylmethylthio)-ethyl]guanidine
(b) N-cyano-N'-methyl-N''-[2-((5-bromo-4-imidazolyl)methylthio)ethyl]guanidine
(c) N-cyano-N'-methyl-N''-[2-((1-methyl-2-imidazolyl)methylthio)ethyl]guanidine
(d) N-cyano-N'-methyl-N''-[2-((2-imidazolyl)methylthio)-ethyl]guanidine
(e) N-cyano-N'-methyl-N''-[2-((2-thiazolyl)methylthio)-ethyl]guanidine
(f) N-cyano-N'-methyl-N''-[2-((3-(1,2,4)-triazolyl)methylthio)ethyl]guanidine
(g) N-cyano-N'-methyl-N''-[2-(3-isothiazolylmethylthio)-ethyl]guanidine
(h) N-cyano-N'-methyl-N''-[2-(3-isoxazolylmethylthio)ethyl]guanidine
(i) N-cyano-N'-methyl-N''-[2-((5-amino-2-(1,3,4)-thiadiazolyl)methylthio)ethyl]guanidine
(j) N-cyano-N'-methyl-N''-[2-((3-methyl-2-pyridyl)methylthio)ethyl]guanidine
(k) N-cyano-N'-methyl-N''-[2-((3-chloro-2-pyridyl)methylthio)ethyl]guanidine
(l) N-cyano-N'-methyl-N''-[2-((3-hydroxy-2-pyridyl)methylthio)ethyl]guanidine
(m) N-cyano-N'-methyl-N''-[2-(4-imidazolylethylthio)ethyl]guanidine

EXAMPLE 7

Substitution of 2-(chloromethyl)oxazole for 4-chloromethyl-5-methylimidazole in the procedure of Example 1 and the procedure of Example 2(ii) leads to the production of N-methyl-N'-[2-(2-oxazolylmethylthio)ethyl]-thiourea and N-cyano-N'-methyl-N''-[2-(2-oxazolylmethylthio)ethyl]guanidine respectively.

EXAMPLE 8

Treatment of 2-pyridinemethanol under basic conditions with
(a) p-toluenesulphonic anhydride
(b) p-nitrobenzoyl chloride
(c) p-chlorobenzoyl chloride
(d) trifluoromethanesulphonyl chloride
(e) methanesulphonyl chloride
(f) diphenylphosphoryl chloride leads to the production of:
(a) 2-pyridylmethyl p-toluenesulphonate
(b) 2-pyridylmethyl p-nitrobenzoate
(c) 2-pyridylmethyl p-chlorobenzoate
(d) 2-pyridylmethyl trifluoromethylsulphonate
(e) 2-pyridylmethyl methanesulphonate
(f) 2-pyridylmethyl diphenylphosphinate and the treatment of these products with N-cyano-N'-methyl-N''-(2-mercaptoethyl)guanidine and sodium ethoxide in ethanol leads to the production of N-cyano-N'-methyl-N''-[2-(2-pyridylmethylthio)ethyl]guanidine.

EXAMPLE 9

Treatment of 2-bromomethyl pyridine with N-cyano-N'-methyl-N''-(2-mercaptoethyl)guanidine and sodium ethoxide in ethanol leads to the production of N-cyano-N'-methyl-N''-[2-(2-pyridylmethylthio)ethyl]guanidine.

What we claim is:

1. A process for the production of a compound of the formula:

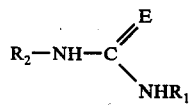

wherein E is sulphur or NCN, $R_1$ is hydrogen or lower alkyl, and $R_2$ is a grouping of the structure $$Het - (CH_2)_m - S - (CH_2)_n -$$

wherein Het is a nitrogen containing 5 or 6 membered heterocyclic ring selected from imidazole, pyridine, thiazole, isothiazole, oxazole, triazole or thiadiazole which ring is optionally substituted by lower alkyl, hydroxyl, halogen or amino; and $m$ is 1 or 2, and $n$ is 2 or 3 such that the sum of $m$ and $n$ is 3 or 4; which comprises treating a compound of the formula

wherein Het and $m$ are as defined hereinabove and Z is a group selected from tosyloxy, methanesulphonyloxy, trifluoromethanesulphonyloxy, benzoyloxy with one or more nitro or chloro substituents, trifluoroacetoxy or diphenylphosphoryloxy, which forms a good leaving group, with a mercaptan of the formula

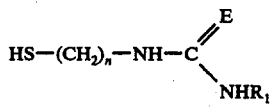

wherein $n$, E and $R_1$ are as defined hereinabove, in the presence of a base, said reactants and base being present in molar equivalent amounts.

2. A process according to claim 1 wherein Z is methanesulphonyloxy or tosyloxy.
3. A process according to claim 1 wherein Het is an imidazole, thiazole, isothiazole or pyridine ring optionally substituted by methyl, chlorine or bromine.
4. A process according to claim 1 wherein $m$ is 1 and $n$ is 2.
5. A process according to claim 1 wherein $R_1$ is methyl.
6. A process according to claim 1 wherein $R_1$ is hydrogen and E is sulphur.
7. A process according to claim 1 wherein $R_1$ is methyl, Het is 5-methyl-4-imidazolyl, $m$ is 1 and $n$ is 2.
8. A process according to claim 7 wherein E in NCN.

* * * * *

UNITED STATES PATENT AND TRADEMARK OFFICE
CERTIFICATE OF CORRECTION

PATENT NO. : 4,093,621

DATED : June 6, 1978

INVENTOR(S) : Thomas Henry Brown, Graham John Durant, John Colin Emmett and Charon Robin Ganellin It is certified that error appears in the above-identified patent and that said Letters Patent are hereby corrected as shown below:

Column 1, line 21, below the structural formula, insert
-- FORMULA I -- .

Signed and Sealed this

Seventh Day of November 1978

[SEAL]

Attest:

RUTH C. MASON
Attesting Officer

DONALD W. BANNER
Commissioner of Patents and Trademarks